United States Patent [19]

Ellard

[11] 4,080,325
[45] Mar. 21, 1978

[54] SYNTHESIS OF METHOTREXATE

[75] Inventor: James A. Ellard, Dayton, Ohio

[73] Assignee: The United States of America as represented by the Department of Health, Education and Welfare

[21] Appl. No.: 742,450

[22] Filed: Nov. 17, 1976

[51] Int. Cl.$^2$ ............................................ C07D 475/08
[52] U.S. Cl. ......................... 260/251.5; 260/256.4 B; 560/41
[58] Field of Search ..................................... 260/251.5

[56] References Cited

U.S. PATENT DOCUMENTS 3,989,703  11/1976  Nicolesco-Duvaz et al. ..... 260/251.5

*Primary Examiner*—Paul M. Coughlan, Jr.
*Attorney, Agent, or Firm*—John S. Roberts, Jr.; Norman J. Latker; Thomas G. Ferris

[57] ABSTRACT

The present invention consists of three process improvements in the so-called multi-step Piper-Montgomery process designed especially to produce the antifolate methotrexate which is closely related to both aminopterin and folic acid. 2,4,5,6-tetraaminopyrimidine sulfite is one starting material and is usually produced in the form of the bisulfite in an acetate buffer. The present modification positively produces the hydrochloride from the bisulfite and eliminates the acetate buffer utilized in prior art processes. Subsequently, a pteridine ring is formed from the pyrimidine hydrochloride using dihydroxyacetone at pH 5.5±0.2 to form the second ring. This strict pH control together with the use of hydrochloride salt minus the acetate buffer assists in preferentially favoring the formation of 2,4-diamino-6-hydroxymethylpteridine. Subsequently the 6-hydroxymethyl compound is converted to the hydrobromide acid salt and reacted with three moles of a triphenyl dibromophosphorane and phosphazine protecting groups are formed on the amine groups of the pteridine ring as the 6-hydroxymethyl group is transformed to 6-bromomethyl, a key intermediate. The present process leaves the protecting phosphazine groups on the primary amino groups to discourage side reactions during subsequent alkylation of the other major reactant, ethyl N-(p-methylaminobenzoyl)-L-glutamate. Furthermore, ethyl N-(p-methylaminobenzoyl)-L-glutamate, the other reactant, is uniquely produced for the present multi-step reaction by a process proceeding from ethyl N-(p-trifluoromethylaminobenzoyl)-L-glutamate by utilizing an alkali metal hydroxide in a lower ($C_1$–$C_6$) alkanol wherein the protective trifluoroacetyl groups are removed. This step uses a special mixture preferably of an alkali metal hydroxide in ethanol and optimally 1 equivalent of KOH in 20% ethanol at or below ambient temperature where the mixture is added slowly to keep the reaction pH below 9. The combination of these improvements results in the increase of an overall yield of methotrexate from the named starting reactants from about 25% to approximately 40–50%.

10 Claims, No Drawings

SYNTHESIS OF METHOTREXATE

The present invention relates to improvements in a process for the production of the compound methotrexate (NSC 740). This compound is structurally reproduced below.

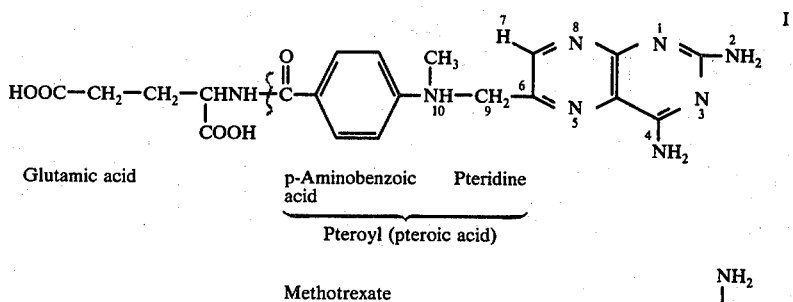

Methotrexate

It is noted from the above formula that methotrexate consists of a glutamate fraction, a p-aminobenzoic acid fraction, and a pteridine fraction. The present invention comprises alkylation of the amino group at the 10 position by adding the pteridine fraction proceeding from the 9 position. In a multi-step process the process generally follows the technique of Piper and Montgomery, *J. Het. Chem.*, 11:279 (1974) with process improvements to increase yield. An outgrowth of the Piper and Montgomery article is Ser. No. 563,466 of Piper, which was filed March 31, 1975, entitled "Method of Making Pteridine Compounds." The application above is incorporated by reference as belonging to a common assignee, Government of the United States, Department of Health, Education and Welfare, and NTIS 242148.

Additionally, of importance in the prior art is the article by Baugh and Shaw, J. Organic Chem., 29:3610 (1964) which teaches the condensation of dihydroxyacetone with 2,6-disubstituted 4,5-diaminopyrimidines, such as 2,4,5,6-tetraaminopyrimidine in sodium acetate buffer.

A key advantage of the present invention is the selection of a pH value that minimizes formation of by-product pteridines, elimination of the sodium acetate or acetate buffer previously used in Baugh and Shaw and in Piper and Montgomery above, and the conversion of the sulfite acid addition salt to hydrochloride salt.

It is further of interest that the two prior art publications above used to hydrochloride form of 2,4,5,6-tetraaminopyrimidine which they derive from the amine sulfate with the reaction of $BaCl_2$. In the prior art, however, there was no monitoring of the pH of the reaction mixture and no record of same. In the reaction scheme below (II), the present inventor uncovered the 7-hydroxymethyl isomer which is an unwanted by-product. This isomer is favored at a high pH while the 6-methylpteridine by-product below is favored at a low pH. The sum of these two major by-products is at a minimum at pH 5.5±0.2. The pH of the reaction mixture is so delicate and critical that serious contamination results if this is varied as much as 0.5 pH unit.

Again, even at the optimum pH of 5.5, which favors the desired 6-hydroxymethylpteridine isomer, isomerization is catalyzed by the presence of acetate sulfite and borate anions and thus the elimination of the acetate buffer was mandatory to improvement of yield.

Proceeding from 2,4,5,6-tetraaminopyrimidine sulfite as a reactant, the conversion in the present process consists of the following step:

II

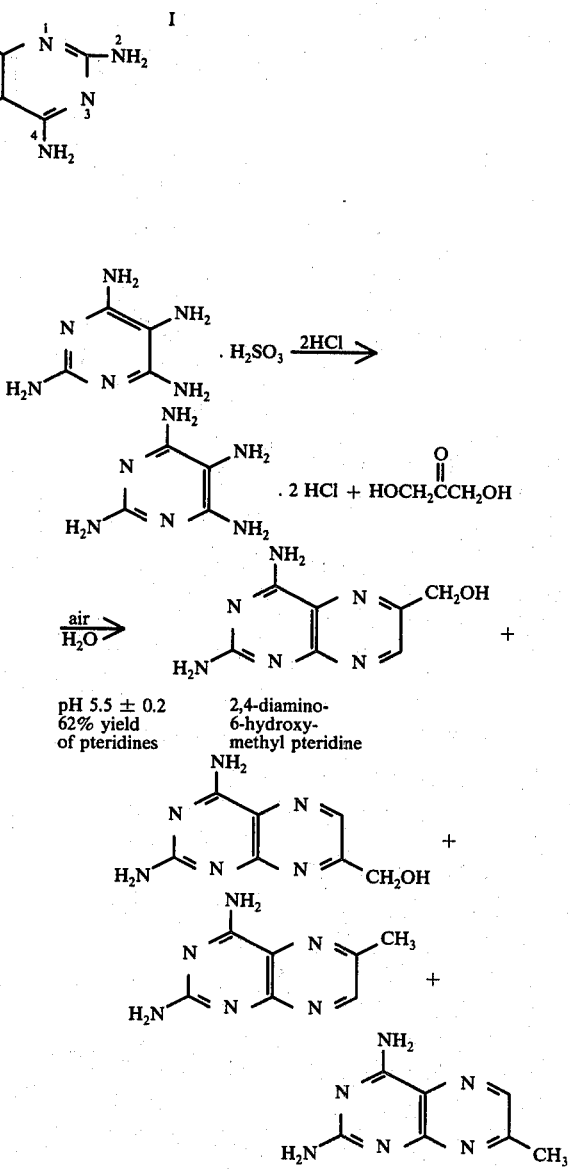

The above equation shows graphically the conversion of amine sulfite to amine hydrochloride. In the later ring closure the conversion to 2,4-diamino-6-hydroxymethylpteridine is favored over the other possible products to a greater extent than in the previous processes.

Piper and Montgomery recognized that the 6-methyl compound was a contaminant and more recently the present inventor has found that the 7-hydroxymethyl compound is also a contaminant. Experimental work has shown that deleterious isomerization is caused in part by divalent anions as sulfite and sulfate as well as the presence of an acetate buffer. In the present invention, the acetate buffer was eliminated and strict pH control at 5.5 ±0.2 was utilized using tetraaminopyrimidine hydrochloride derived from tetraaminopyrimidine sulfite and this procedure gave increased yield of the preferred 6-hydroxymethylpteridine.

Additionally, in the process it has proved advantageous to brominate the 6-position or convert the hydroxymethyl compound to bromomethyl by means of triphenyl dibromophosphorane which, at the same time, forms protecting phosphazine groups at the 2 and 4 position on the primary amines and forms a CH₂Br at the 6-position according to the following equation:

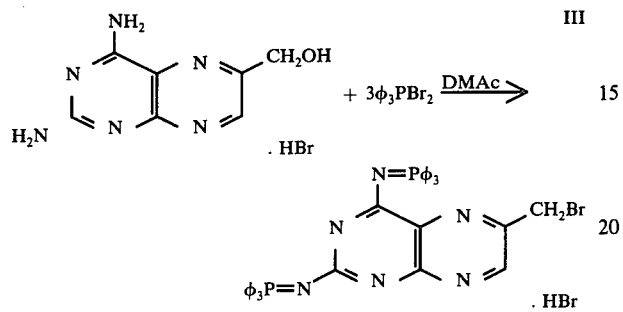

The reaction on the primary amine groups of the 2,4-diaminopteridine forms a nitrogen/phosphorus bond which protects those amines during subsequent alkylation reaction. This allows coupling of the ester to a much higher degree of conversion than would have been accomplished without this protection. The HBr salt is also formed in the presence of excess HBr.

Separately the fraction of the methotrexate molecule involving the p-aminobenzoyl glutamate is prepared from 4[(N-methyl)-trifluoroacetamido]benzoyl-L-glutamic acid diethyl ester by removing the trifluoroacetyl groups by means of an equivalent of an alkali metal hydroxide in a lower (C₁–C₆) alkanol at or below ambient temperature. A specially preferred mixture utilizes alkali metal hydroxide in ethanol and optimally a mixture of 1 equivalent of KOH in 20% ethanol is utilized.

The mixture is added slowly to maintain a pH of the solution below about 9 according to the following equation:

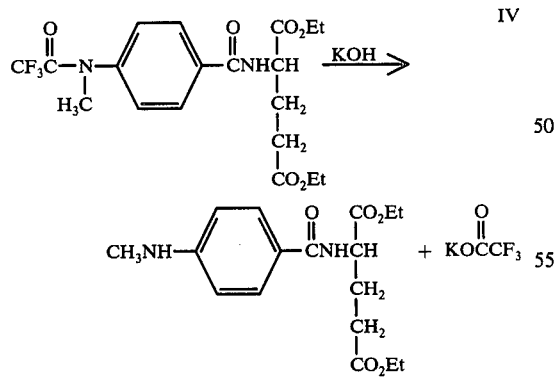

Under these conditions the hydrolysis and racemization of the ester are slow enough to be almost undetectable and the reaction is complete within about 30 minutes. Previously, no difficulty had been encountered in removing trifluoroacetyl protective groups from amino acids but application of this reaction to esters of amino acids was limited by the simultaneous hydrolysis of the ester function.

It is preferred that the phosphazine be stabilized at about 50° C in the presence of excess dry HBr utilized in DMAC (dimethylacetamide). At least 3 moles of triphenyl dibromophosphorane are necessary for quantitative conversion.

The N-(p-methylaminobenzoyl)-L-glutamate diethyl ester produced above is now alkylated in the presence of phosphazine groups protecting the primary amines on the pteridine ring to produce methotrexate ester as set out below (Equation V). This is the major coupling reaction of the sequence and differs from the prior art as in Piper where the protecting groups were removed by destroying the excess of triphenyl dibromophosphorane before the alkylation. The presence of the protecting groups serves to avoid alkylation of the primary amine groups during the alkylation of ethyl-N-(p-methylaminobenzoyl)-L-glutamate.

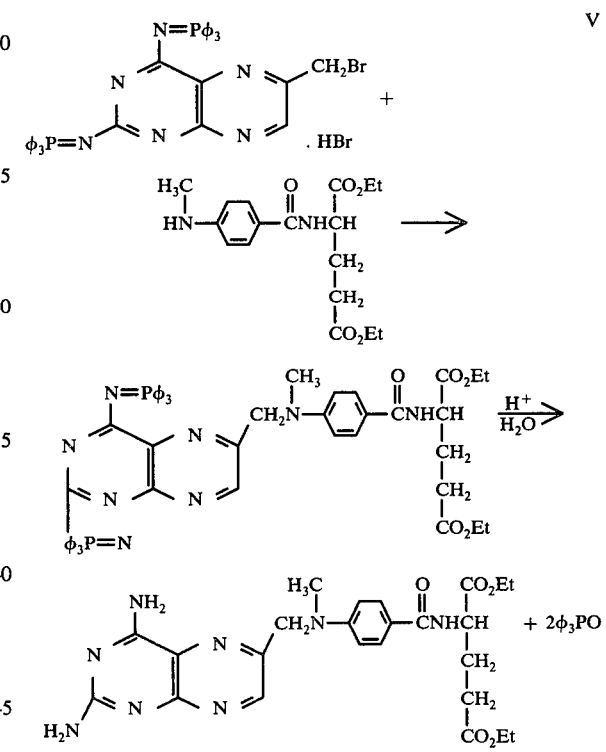

Subsequently said methotrexate ester is hydrolyzed to produce methotrexate.

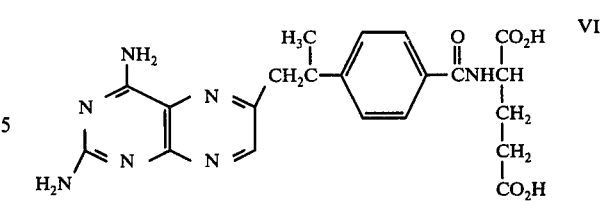

EXAMPLE 1

Improved Synthesis of 2,4-Diamino-6-Hydroxymethylpteridine

In the production Equation I, tetraaminopyrimidine sulfite was reacted with 2 equivalents of hydrochloric acid to give a pale yellow solution which is stable at room temperature for at least 24 hours at a pH value between 1 and 5. This solution was filtered under vacuum to remove as much SO₂ as possible, adjusted to pH 5.5, treated with an excess of dihydroxyacetone and aerated vigorously at room temperature for 12–24 hours. The product conversion was measured by the HPLC of pteridine and pyrimidine peaks. The pH of the reaction mixture was maintained between 5.3 and 5.5 by addition of NaOH until the end of the reaction of the product was recovered by precipitation at pH 5–6, preferably about 5.5. This procedure eliminated the sodium acetate buffer previously used by Baugh and Shaw, *J. Organic Chem.*, 29:3610 (1964) as well as the isomerization caused by buffer ions in the previously published work of Piper and Montgomery, *J. Het. Chem.*, 11:279 (1974). The preparation of the tetraaminopyrimidine sulfite, which is the starting material, was as noted in Traube, *Ber.*, 37:4544.

EXAMPLE 2

Conversion of 2,4-Diamino-6-Hydroxymethylpteridine to the 6-Bromomethyl Derivative 2,4-diamino-6-hydroxymethylpteridine was added to at least 3 moles of triphenyl dibromophosphorane in dry DMAC below 10° C. The excess of triphenyl dibromophosphorane was consumed in reaction with the amino groups to form phosphazines. The addition of the 3 moles of phosphorane protects the amine groups of the pteridine rings from side reactions, permits the reaction to go cleanly in good yield, and simplifies purification of the reaction products. The reaction took place at temperatures below about 20° C in the presence of excess dry HBr in dimethylacetamide (DMAC). The product is the 2,4-bis(triphenylphosphazino)-6-bromomethylpteridine, which is used later in the alkylation of ethyl N-(p-methylaminobenzoyl)-L-glutamate.

EXAMPLE 3

Removal of Trifluoroacetyl Protective Groups from 4[(N-methyl)trifluoroacetamido]benzoyl-L-glutamic acid diethyl ester The trifluoroacetyl groups residing on 4[(N-methyl)-trifluoroacetamido]benzoyl-L-glutamic acid diethyl ester were removed easily by adding a stoichiometric equivalent of KOH in aqueous ethanol to a solution of the ester in ethanol at or below ambient temperature. The addition was made slowly enough to maintain the pH of solution below about 9. Under these circumstances, hydrolysis and racemization of the ester are slow enough to be almost undetectable and the reaction was complete in about 30 minutes. The reaction was titrated to an end point by measuring the concentration of unhydrolyzed trifluoroacetamido derivative by either HPLC or TLC.

EXAMPLE 4A

Preparation of Ethyl N-[p-(Methylamino)Benzoyl]-L-Glutamate

The 310 pounds of wet ethyl N-[p-(trifluoroacetamido)-benozyl]-L-glutamate were added to 65 gallons of methylene chloride in reactor 1, a 100 gallon glass-lined reactor. After stirring and settling the methylene water separated and was decanted. The methylene chloride layer was stripped to 30 gallons at 40° internal temperature and partial vacuum. 40 gallons of tetrahydrofuran was added and the mixture was stripped to about 35 gallons. At this time the last of the distillate showed 1.03% methylene chloride by GC analysis. Karl Fisher analysis confirmed less than 0.1% moisture.

The volume was brought to 77 gallons in a second reactor 2 with tetrahydrofuran and 55 pounds of granular anhydrous potassium carbonate was added along with 113¼ pounds of methyl iodide. The slurry was stirred overnight at 55° C, however, the reaction did not go to completion so 50 pounds of powdered anhydrous potassium carbonate was added and the reaction went to completion within 12 hours at 55°.

The reaction mixture was then filtered on a Sparkler filter and stripped in reactor 2 to a volume of 40 gallons, first with no vacuum then using partial vacuum. The last distillate contained 2% CH₃I. Denatured alcohol was added, then 20 gallons was distilled off under vacuum. Eighteen pounds of potassium hyroxide dissolved in 6 gallons of water and 12 gallons of ethanol was metered into reactor 2 over a period of 1½ hours at which point the hydrolysis was complete and the pH was adjusted to 7.0.

25 gallons of deionized water and 25 gallons of benzene was then added into reactor 2. The mixture was stirred and the benzene layer was decanted. The water layer was twice again extracted, each time with 12½ gallons of benzene. The benzene extracts were combined and washed first with 12½ gallons of a 5% sodium chloride in water solution, then with 12½ gallons of deionized water. The benzene extract was then stripped to 25 gallons volume in reactor 1. To this 25 gallons of hexane was added and the contents were cooled at 15° C. The precipitate which formed was filtered and dried in a vacuum oven overnight. The net yield was 72 pounds (64.5% based on the ethyl p-aminobenzoyl-L-glutamate used), mp 88°–89° corrected.

| Optical Rotation | C = 1.03/95% EtOH | C = 1.02/1N HCl |
|---|---|---|
| $[\alpha]_{D}^{25}$ | − 9.39° | −23.9° |
| $[\alpha]_{578}^{25}$ | − 9.43° | −20.5° |
| $[\alpha]_{546}^{25}$ | −10.11° | −22.5° |
| $[\alpha]_{436}^{25}$ | −13.07° | −38.9° |

EXAMPLE 4B

Preparation of Methotrexate Ester

Into a 100-gallon glass-lined reactor (1), 53 gallons of dimethylacetamide, which had 0.09% moisture, was charged. To this 118 pounds of triphenyl phosphine was charged. The batch was cooled to 0° C. A drum of bromine was set on a scale and connected to the reactor charge line. A total of 72 pounds of bromine was pressurized into the reactor in increments over a period of 4 hours. The bromine was added to maintain the batch temperature between 0° C and 4° C.

A total of 41 pounds of pure 2,4-diamino-6-hydroxymethylpteridine hydrobromide was charged into the reactor. The temperature warmed to 8° C and was then cooled to 4° C. The temperature was then raised to 21° C over the next 12 hours. At this point HPLC showed that 87.3% of the hydroxymethylpteridine had been converted to bromomethylpteridine.

Ethyl N-(p-methylamino)benzoylglutamate, 55 lbs, was charged to the reaction mixture and the temperature was raised to 45° C. After holding the batch for 22 hours, an additional 7 lbs of ethyl N-(p-methylamino)-benzoylglutamate was added. After an additional 10 hours conversion peaked at 52.3% methotrexate ester (based on total pteridines) and the mixture was cooled.

Then 450 gallons of deionized water was charged into a separate reactor (2). The pH was adjusted to 1.5 with hyrochloric acid and 15° C cooling water was applied to the reactor jacket. With the agitator running on the separate reactor (2) the entire reaction mixture was pressurized from reactor 1 into reactor 2 over a period of about 1½ hours. A precipitate immediately formed. After agitating for ½ hour and checking the pH at 1.2, the slurry was filtered. The filtrate was pumped to a 500-gallon stainless reactor (3), the solids, consisting primarily of triphenylphosphine oxide, were set aside. The filtrate was immediately drained back into reactor 2 and adjusted to pH 3 using 6N sodium hydroxide. Solids began to precipitate at a pH of 2.4. A minimum of agitation was used. The solids were then filtered on a U.S. Stoneware filter. The filtrate was returned to reactor 2 for recovery of additional ester.

The 105 pounds of wet methotrexate ester collected at pH 3 was purified as follows. 63 gallons of methanol was charged into reactor 2. The wet solids were then charged to reactor 2 and a total of 1567 ml of hydrochloric acid was used to dissolve the solids. Then 235 gallons of water was added and pH was adjusted to 3.0 with 2N sodium hyroxide. The solids were filtered on a U.S. Stoneware filter yielding a total of 88 pounds of wet cake. This represents about 50 pounds of methotrexate ester.

I claim:

1. A process for the preparation of methotrexate comprising the following steps:
    a. reacting tetraaminopyrimidinehydrochloride with dihydroxyacetone in the presence of air and water and at a pH in the range of 5.5±0.2 to give 2,4-diamino-6-hydroxymethylpteridine;
    b. converting the 2,4-diamino-6-hydroxymethylpteridine to the hydrobromide salt, namely 2,4-diamino-6-hydroxymethylpteridine.hydrobromide salt;
    (c) reacting the 2,4-diamino-6-hydroxymethylpteridine.hydrobromide salt with triphenyldibromophosphorane to give 2,4-bis(triphenylphosphazine)-6-bromomethylpteridine.hydrobromide;
    (d) reacting the 2,4-bis(triphenylphosphazino)-6-bromomethylpteridine.hydrobromide with ethyl N-(p-methylamino)benzoylglutamate to give the phosphazino derivative of methotrexate ester;
    (e) hydrolyzing the phosphazino derivative of methotrexate ester to give triphenylphosphine oxide and methotrexate ester; and,
    (f) hydrolyzing the methotrexate ester to give methotrexate.

2. A process of claim 1 wherein said tetraaminopyrimidine.hydrochloride is made by a process comprising reacting 2,4,5,6-tetraminopyrimidine.sulfite with hydrochloric acid at pH of 1 to 5 to give tetraminopyrimidinehydrochloride and sulfur dioxide.

3. A process of claim 2 wherein said ethyl N(p-methylamino)benzoylglutamate is made by a process comprising reacting 4[(N-methyl)trifluoroacetamide]-benzoyl-L-glutamic acid diethyl ester with an alkali metal hydroxide in an aqueous lower alkanol at a pH of ≳9 to give ethyl N(p-methylamino)benzoylglutamate.

4. A process of claim 3 wherein said alkali metal hydroxide comprises potassium hydroxide.

5. A process of claim 4 comprising using 1 equivalent of potassium hydroxide in aqueous ethanol to effect the removal of the trifluoroacetyl groups.

6. A process of claim 5 comprising using 1 equivalent of potassium hydroxide in 20% ethanol to effect the removal of the trifluoroacetyl groups.

7. A process of claim 1 comprising carrying out steps (c) and (d) in the presence of dimethylacetamide reaction medium.

8. A process of claim 1 comprising in step (c) adding the triphenyldibromophosphorane at a temperature of ≲10° C to the 2,4-diamino-6-hydroxymethylpteridine.hydrobromide salt and completing the reaction at a temperature of ≲20° C.

9. A process of claim 8 comprising adding 3 moles of the triphenyldibromophosphorne per mole of the 2,4-diamino-6-hydroxymethylpteridine.hydrobromide salt.

10. A process of claim 1 comprising carrying out steps (c) and (d) in the presence of dimethylacetamide reaction medium, and in step (c) adding at a temperature of ≲10° C 3 moles of triphenyldibromophosphorane per mole of 2,4-diamino-6-hydroxymethylpteridine.hydrobromide salt and completing the reaction at a temperature of ≲20° C.

* * * * *